United States Patent
Piantoni et al.

(10) Patent No.: US 10,751,225 B2
(45) Date of Patent: Aug. 25, 2020

(54) MACHINE AND METHOD FOR MAKING ABSORBENT SANITARY ARTICLES

(71) Applicant: GDM S.p.A., Bologna (IT)

(72) Inventors: Matteo Piantoni, Albino (IT); Valerio Soli, Bologna (IT)

(73) Assignee: GDM S.P.A., Bologna (IT)

(*) Notice: Subject to any disclaimer, the term of this patent is extended or adjusted under 35 U.S.C. 154(b) by 854 days.

(21) Appl. No.: 14/784,508

(22) PCT Filed: Apr. 8, 2014

(86) PCT No.: PCT/IB2014/060527
§ 371 (c)(1),
(2) Date: Oct. 14, 2015

(87) PCT Pub. No.: WO2014/170797
PCT Pub. Date: Oct. 23, 2014

(65) Prior Publication Data
US 2016/0051414 A1    Feb. 25, 2016

(30) Foreign Application Priority Data

Apr. 17, 2013   (IT) .............................. BO2013A0174

(51) Int. Cl.
*A61F 13/15*      (2006.01)
*A61F 13/53*      (2006.01)
(Continued)

(52) U.S. Cl.
CPC .. *A61F 13/15772* (2013.01); *A61F 13/15634* (2013.01); *A61F 13/534* (2013.01);
(Continued)

(58) Field of Classification Search
None
See application file for complete search history.

(56) References Cited

U.S. PATENT DOCUMENTS

| 4,735,673 A | 4/1988 | Piron |
| 6,059,710 A | 5/2000 | Rajala et al. |
| (Continued) |

FOREIGN PATENT DOCUMENTS

| DE | 19805335 A1 | 8/1999 |
| EP | 2345395 A1 | 7/2011 |
| (Continued) |

OTHER PUBLICATIONS

Machine Translation of JP 2008-154964 A, dated Sep. 14, 2018 (Year: 2018).*
(Continued)

*Primary Examiner* — Benjamin A Schiffman
(74) *Attorney, Agent, or Firm* — Shuttleworth & Ingersoll, PLC; Timothy J. Klima (57) ABSTRACT

A machine for making absorbent sanitary articles including an absorbent pad with at least one discrete layer of superabsorbent polymer material includes a unit for forming and applying a succession of absorbent pads, which includes a drum for forming the pad, a duct for feeding a charge of superabsorbent polymer material to the drum and intermittent valve mounted along a stretch of the duct and driven by an actuator. A device detects the superabsorbent polymer material and sends a signal to a control and drive unit connected to the device indicating that the superabsorbent polymer material has been detected. The control and drive unit is configured to drive the actuator to bring the valve into phase with the rotation of the drum when the deviation of the signal from a reference signal exceeds a defined threshold value.

6 Claims, 4 Drawing Sheets

(51) Int. Cl.
*A61F 13/534* (2006.01)
*G01N 22/04* (2006.01)

(52) U.S. Cl.
CPC .............. *A61F 2013/15788* (2013.01); *A61F 2013/15796* (2013.01); *A61F 2013/53051* (2013.01); *A61F 2013/530481* (2013.01); *A61F 2013/530532* (2013.01); *G01N 22/04* (2013.01)

(56) References Cited

U.S. PATENT DOCUMENTS

| | | | |
|---|---|---|---|
| 6,242,074 | B1 | 6/2001 | Thomas |
| 6,527,902 | B1 | 3/2003 | Rajala |
| 8,677,930 | B2 * | 3/2014 | Pastrello ................. B05B 7/144 118/504 |

FOREIGN PATENT DOCUMENTS

| | | |
|---|---|---|
| EP | 2540267 A1 | 1/2013 |
| JP | 2008154964 A | 7/2008 |
| JP | 2011120757 A | 6/2011 |
| JP | 2011177299 A | 9/2011 |
| JP | 2012011235 A | 1/2012 |
| WO | WO0012974 A1 | 3/2000 |
| WO | 0156522 A1 | 8/2001 |
| WO | WO03062839 A1 | 7/2003 |
| WO | WO2009073849 A1 | 6/2009 |
| WO | 2010103444 A1 | 9/2010 |
| WO | WO2010103453 A1 | 9/2010 |

OTHER PUBLICATIONS

Japanese Office Action dated Apr. 3, 2018 from counterpart Japanese App No. 2016-508259.
Notice of Opposition of European Patent No. 14722356.4 dated Mar. 5, 2018.
Merriam-Websters Collegiate Dictionary, Tenth Edition, Merriam-Webster, Incorporated, p. 1305, definition of "Valve".
Hossbach Sensor Technologie, Sensor Equipment for Production and Quality Control, Catalogue 2008, pp. 1, 3, 8, 15, 60 and 62.
International Search Report and Written Opinion dated Oct. 6, 2014 for related PCT Application No. PCT/IB2014/060527.
Letter from Opponent dated Jul. 11, 2019 in Opposition Proceedings in European Patent No. 14722356.4.

* cited by examiner

MACHINE AND METHOD FOR MAKING ABSORBENT SANITARY ARTICLES

This application is the National Phase of International Application PCT/IB2014/060527 filed Apr. 8, 2014 which designated the U.S. and that International Application was published under PCT Article 21(2) in English.

This application claims priority to Italian Patent Application No. BO2013A000174 filed Apr. 17, 2013, which application is incorporated by reference herein.

TECHNICAL FIELD

This invention relates to a machine and a method for making absorbent sanitary articles.

BACKGROUND ART

As is known, nappies comprise an impermeable layer, for example of polyethylene, a layer of non-woven fabric permeable to liquids and an absorbent pad sandwiched therebetween.

Absorbent pads are made mainly from natural fibre material (known as "fluff") uniformly blended with superabsorbent polymer material ("SAP").

In order to increase pad absorption capacity absorbent pads have been developed which comprise one or more discrete absorbent layers made mainly from superabsorbent polymer material ("SAP").

It is known from the prior art that a unit for making absorbent pads for nappies comprises a drum, which rotates about its axis of rotation and which has on its peripheral cylindrical surface a plurality of suction housings or recesses within which respective absorbent pads are formed.

The unit also comprises a hood which is used for feeding fluff mixed with "SAP" and which is located to face the peripheral cylindrical surface of the drum.

The fluff and "SAP" are fed pneumatically into the hood and, once mixed, settle in the suction recesses formed on the drum and located to face the hood.

It is also known that the unit comprises a feeding duct having a mouth for delivering charges of superabsorbent material ("SAP") used to define the above mentioned discrete absorbent layers.

Intermittent valve means regulate the feed flow of the feeding duct as a function of the spacing of the drum recesses, so that discrete charges of superabsorbent polymer material ("SAP") are delivered exactly at the moment a suction recess of the drum comes to face the delivery mouth of the duct itself.

It has been found, however, that on account of incorrect manual settings or mechanical malfunctions, the intermittent valve means go out of phase with the rotation of the drum and, consequently, the feeding duct does not deliver the discrete charges of superabsorbent polymer material when a suction recess only partly faces the duct delivery mouth or does not face the duct delivery mouth.

This leads to the formation of defective absorbent pads because the discrete layers of superabsorbent polymer material in the respective pad are not positioned correctly relative to a reference position.

The incorrect position of the discrete layers of superabsorbent polymer material reduces the effective liquid absorbing capacity of the absorbent pad.

AIM OF THE INVENTION

This invention has for an aim to provide a machine and a method for making absorbent sanitary articles, as disclosed herein, and which can overcome the above mentioned disadvantages of the prior art.

BRIEF DESCRIPTION OF THE DRAWINGS

The invention will now be described with reference to the accompanying drawings which illustrate a non-limiting embodiment of it and in which.

DETAILED DESCRIPTION OF PREFERRED EMBODIMENTS OF THE INVENTION

Figure 1:
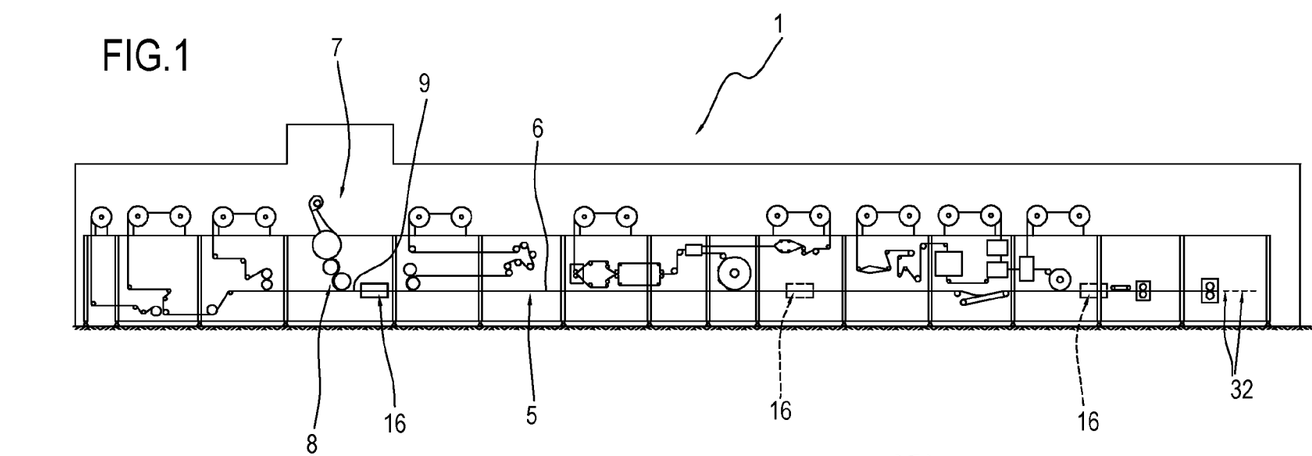
FIG. 1 is a schematic front view illustrating a machine for making absorbent sanitary articles according to this invention.

With reference to FIG. 1, the numeral 1 denotes in its entirety a machine for making absorbent sanitary articles 32 which comprise a sheet of permeable material and a sheet of impermeable material having, sandwiched between them, an absorbent pad 2 constituting the part of the absorbent sanitary article 32 whose function is to absorb liquids.

The absorbent pad 2 comprises at least a first absorbent material 37.

Preferably, the first absorbent material 37 is made mainly from natural fibre material (fluff) 3 uniformly blended with superabsorbent polymer material ("SAP") 4

Alternatively the absorbent pad 2 is made mainly or only from natural fibre material (fluff) 3 or superabsorbent polymer material ("SAP") 4.

The absorbent pad 2 also comprises at least one discrete layer 19 of superabsorbent polymer material ("SAP") 4b defining a second absorbent material 38.

Preferably, the superabsorbent polymer material 4, 4b used is superabsorbent polymer material in granular form.

The machine 1 comprises a line 5 for feeding at least one continuous web 6 of impermeable material used to make the above mentioned sheet of impermeable material.

The machine 1 comprises a unit 7 for forming and applying a succession 8 of absorbent pads 2 and located along the feed line 5.

More specifically, the unit 7 is substantially tangent to the feed line 5 at a release station 9.

The unit 7 comprises a forming drum 10 by which the absorbent pads 2 are formed.

The drum 10 is substantially tangent to the feed line 5 at the release station 9.

The drum 10 has a horizontal axis of rotation perpendicular to the feed line 5.

On its peripheral surface, the drum 10 has one or more suction recesses 11.

The suction recesses 11 are located on the peripheral surface of the drum 10 at a predetermined spacing P.

As the drum 10 rotates, absorbent pads 2 are gradually formed inside respective suction recesses 11 and, once completed, are released onto the feed line 5 by the drum 10 itself at the release station 9.

The unit 7 comprises a hood 12 which is mounted in such a way as to peripherally face at least part of the peripheral surface of the drum 10.

More specifically, the hood 12 feeds the forming drum 10.

The unit 7 comprises a first system 32 for metering the natural fibre material (fluff) 3 and a second system 33 for metering the superabsorbent polymer material ("SAP") 4 of the first absorbent material 37.

Figure 5:
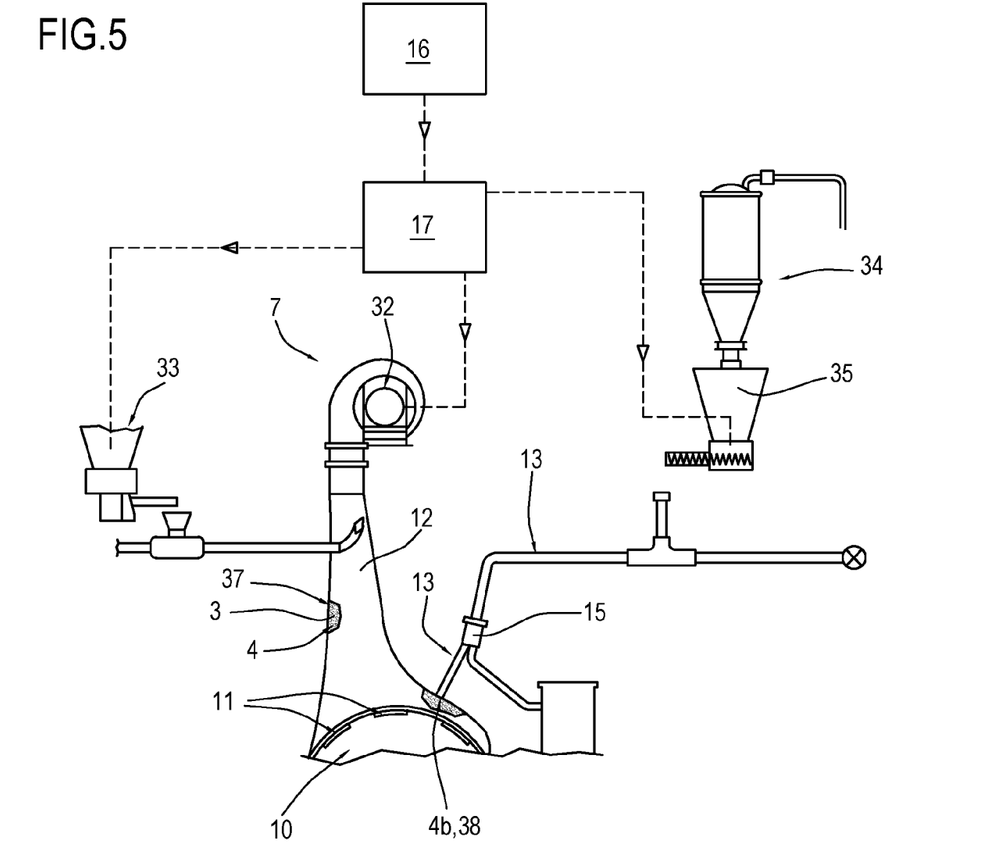
FIG. 5 is a schematic front view of a detail of the machine of FIG. 1.

The unit 7 also comprises a third system 34 for metering the superabsorbent polymer material ("SAP") 4b defining the discrete layer 36 of the absorbent pad 2, as illustrated in FIG. 5.

The first, second and third metering systems 32, 33, 34 are preferably connected to the feed hood 12.

The third metering system 34 comprises at least one metering device 35 and one feeding duct 13 connected to the metering device 35 at the outfeed of the metering device 35 itself.

More precisely, the duct 13 has a delivery mouth 14 leading to the hood 12.

The feeding duct 13 comprises valve means 15 driven by an actuator unit 20.

The valve means 15 are located upstream of the delivery mouth 14 along a stretch of the feeding duct 13.

More specifically, the valve means 15 define a first stretch T1 of the duct 13 upstream of the valve means 15 and a second stretch T2 of the duct 13 downstream of them.

The valve means 15 deliver charges of superabsorbent polymer material intermittently into the feeding duct 13, in particular into the second stretch T2 of the feeding duct 13.

More precisely, the valve means 15 deliver charges of superabsorbent polymer material 4 intermittently as a function of the spacing P of the suction recesses 11 of the drum 10.

Thus, the feeding duct 13 delivers charges of superabsorbent polymer material 4 when a suction recess 11 is facing the delivery mouth 14 of the duct 13 itself.

It should be noted that correct phasing between the valve means 15 and the position of the recesses 11 of the drum 10 guarantees correct positioning of the discrete layers 19 of superabsorbent polymer material in the recesses 11 of the drum 10 and, hence, in the absorbent pad 2.

In effect, in order to guarantee optimal liquid absorption, the discrete layer 19 is located at a predetermined reference position in the absorbent pad 2.

The unit 7 comprises at least one device 16 for detecting the superabsorbent polymer material 4 located downstream of the valve means 15 and a control and drive unit 17 connected to the detecting device 16.

More specifically, the detecting device 16 sends a detection signal 18 each time the detection signal 16 detects the superabsorbent polymer material 4 defining the discrete layer 19.

The control and drive unit 17 is configured to acquire the detection signal 18 and to compare it with a predetermined reference signal 19.

Based on the deviation between the detection signal 18 and the reference signal 19, the control and drive unit 17 is configured to drive the actuator unit 20 of the valve means 15 to bring the valve means 15 into phase with the rotation of the forming drum 10.

Figure 2:
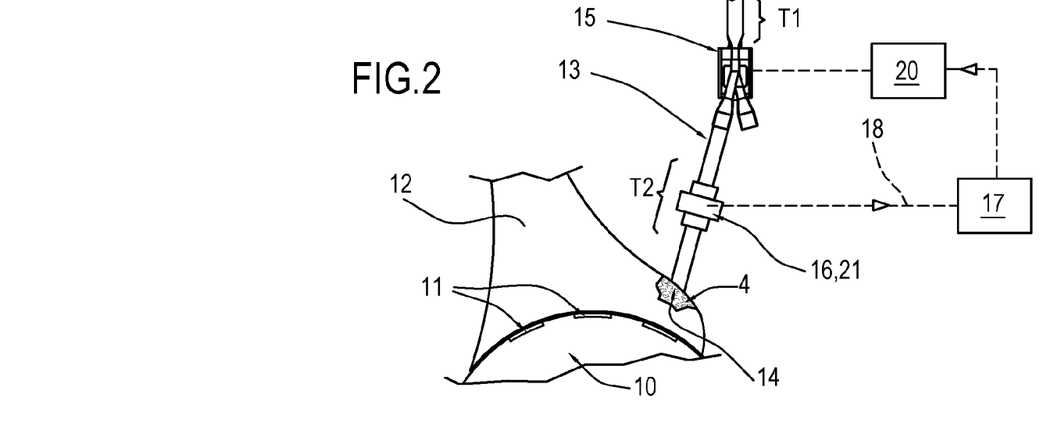
FIG. 2 is a schematic front view of a detail of a first embodiment of the machine of FIG. 1.

In a first embodiment, the detecting device 16 is configured to detect the passage of each charge of superabsorbent polymer material 4 in the feeding duct 13, in particular in the second stretch T2, and to send the detection signal 18 to the control and drive unit 17.

It should be noted that since feed by the valve means 15 is intermittent, the detecting device 16 detects the superabsorbent polymer material 4 in the feeding duct 13 intermittently.

In this case, the reference signal 19 of the control and drive unit 17 is a sync signal of the drum 10 which forms the absorbent pads 2.

The control and drive unit 17 compares the detection signal 18 with the sync signal of the drum 10 and is configured to drive the actuator unit 20 into phase with the sync signal of the drum 10 if the deviation between the detection signal 18 and the reference signal 19 is such that the valve means 15 are not in phase with the forming drum 10.

The detecting device 16 comprises a microwave resonator 21 which at least partly faces the inside of the feeding duct 13.

More specifically, the detecting device 16 comprises a microwave resonator 21 which at least partly faces the inside of the second stretch T2 of the feeding duct 13.

In an alternative embodiment not illustrated, the detecting device 16 is mounted along the feeding duct 13 upstream of the valve means 15. In this case, the metering device 35 feeds the charge of superabsorbent polymer material 4b into the feeding duct 13 intermittently and the detecting device 16 detects its passage before it enters the valve means 15.

Figure 3:
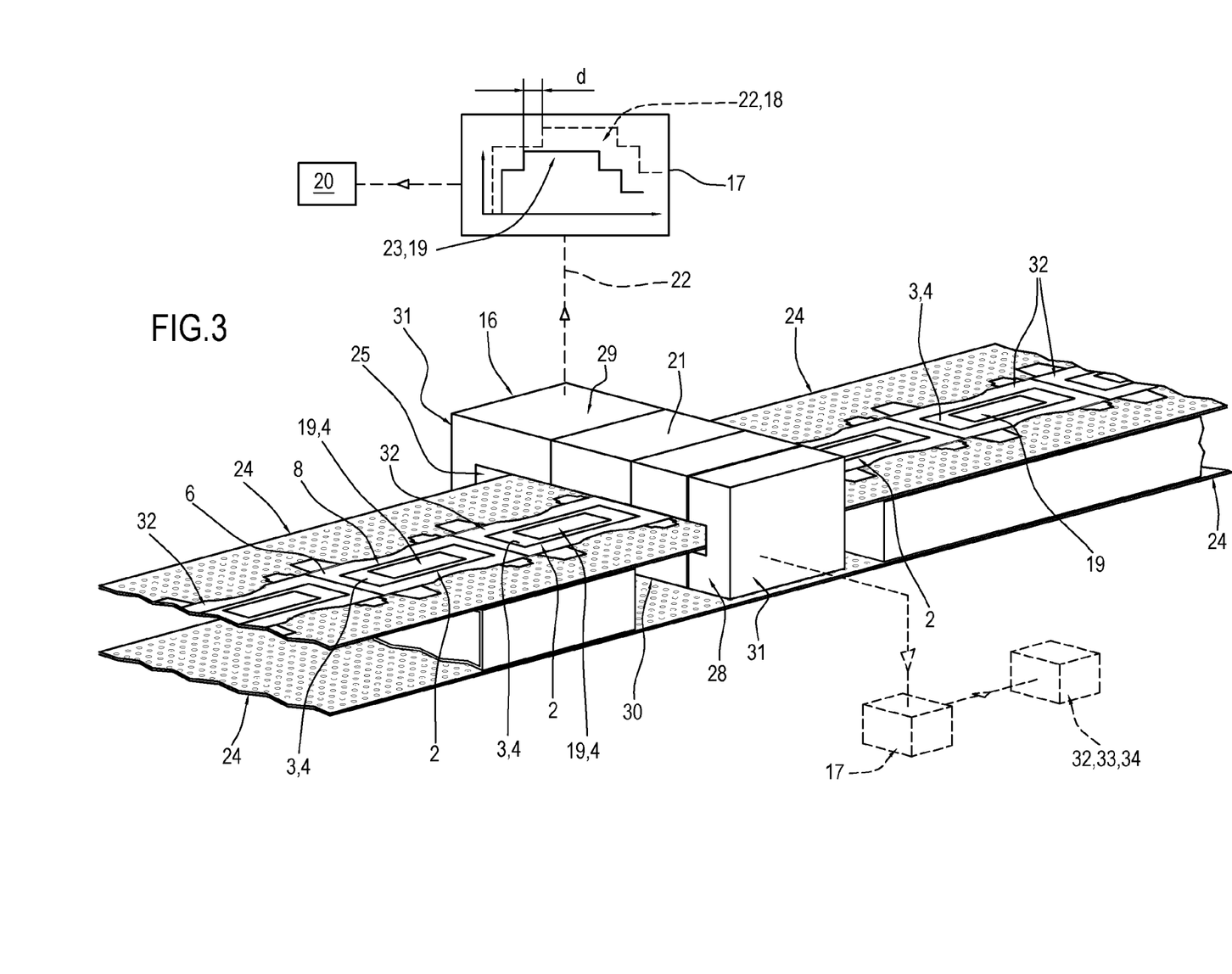
FIG. 3 is a schematic perspective view of a detail of a second embodiment of the machine of FIG. 1.
Figure 4:
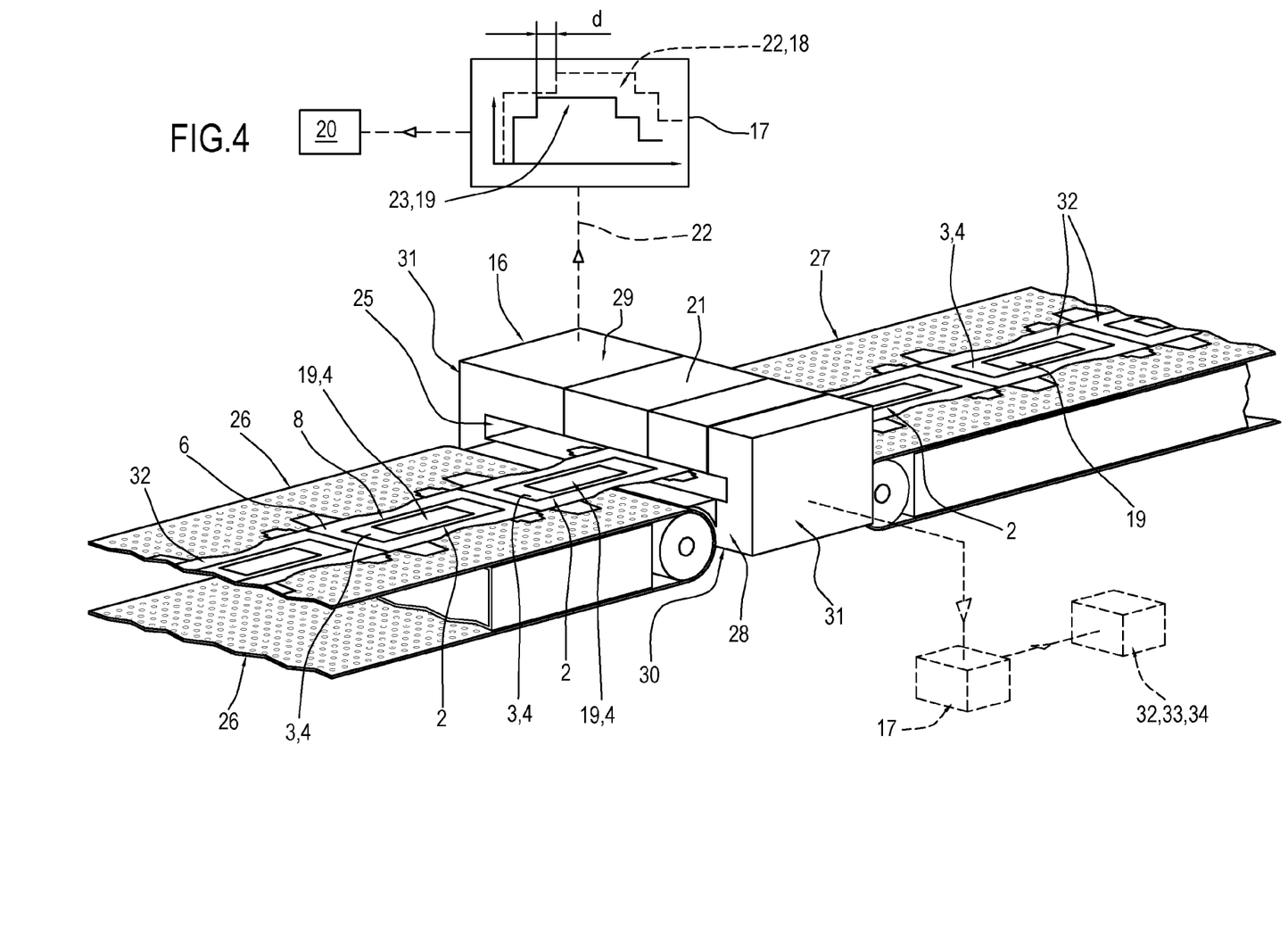
FIG. 4 is a schematic perspective view of a detail of a third embodiment of the machine of FIG. 1.

In a second and a third embodiment, the device 16 for detecting the absorbent pad 2 is mounted along the feed line 5 downstream of the unit 7 for forming and applying the succession 8 of absorbent pads 2.

In this case, the detecting device 16 is configured to detect the position 22 of the discrete layer 19 of superabsorbent polymer material 4 inside the absorbent pad 2.

By detected position 22 is meant the profile of the discrete absorbent layer 19 along a main longitudinal direction of extension of the absorbent pad 2.

The device 16 for detecting the absorbent pad 2 sends the detected position 22 of the discrete layer 19 of superabsorbent polymer material 4 to the control and drive unit 17.

The control and drive unit 17 compares the position 22 detected by the detecting device 16 with a reference position 23 and calculates the deviation "d" between the detected position 22 and the reference position 23.

The control and drive unit 17 is configured to drive the actuator unit 20 and to bring the valve means 15 into phase with the rotation of the forming drum 10 as a function of the deviation "d".

The detecting device 16 comprises a microwave resonator 21 which at least partly faces the succession 8 of the absorbent pads 2 advancing along the feed line 5.

In the second embodiment of the machine 1, as illustrated in FIG. 3, the feed line 5 comprises at least one stretch where the feed line 5 comprises a single conveyor belt 24 for conveying the continuous web 6 of impermeable material.

The detecting device 16 is located along that stretch of the feed line 5.

The detecting device 16 has a slot 25 through which at least the conveyor belt 17 and the succession 8 of absorbent pads conveyed thereby pass in and out More precisely, and preferably, the detecting device 16 is crossed by the conveyor belt 24, by the continuous web 6 of impermeable material and by the succession 8 of absorbent pads 2.

The microwave resonator 21 is positioned to face the conveyor belt 24 and the succession 8 of absorbent pads 2.

In the third embodiment, as illustrated in FIG. 4, the feed line 5 comprises at least one stretch having a first and a second conveyor belt 26 and 27 for conveying the continuous web 6 of impermeable material.

The detecting device 16 is interposed between the first and second conveyor belts 26 and 27 in such a way that at least the continuous web 6 of impermeable material and the succession 8 of absorbent pads 2, conveyed by the first and second belts 26 and 27, pass through the detecting device 16.

Thus, the continuous web 6 of impermeable material and the succession 8 of absorbent pads 2 pass in and out through the slot 25 of the detecting device 16

The microwave resonator 21 is located to face the continuous web 6 of impermeable material and the succession 8 of absorbent pads 2.

In other words, the third embodiment differs from the second embodiment in that no conveyor belt 26, 27 transporting the continuous web 6 of impermeable material passes through the detecting device 16.

To allow the detecting device 16 to be mounted easily along the feed line 5, the detecting device 16 comprises at least one removable element 28.

More specifically, once the removable element 28 has been removed, the conveyor belt 24 and/or the continuous web 6 of impermeable material, depending on the embodiment of the machine 1, can be inserted into the slot 25 of the detecting device 16.

It should be noted that to properly inspect the absorbent pad 2, the detecting device 16 must be calibrated to detect only the superabsorbent polymer material 4 making up the discrete layers 19 of the pad 2.

To calibrate the detecting device 16, it is necessary to make the elements to be excluded during detection of the position 22 of the discrete layers 19 of the absorbent pad 2 pass through the detecting device 16.

The detecting device 16 is preferably calibrated during start-up of the machine 1.

Thus, during the steady-state operation of the machine 1, the detecting device 16 excludes from detection the resonance curves relating to the components of the absorbent article 32 being formed along the feed line 5, with the exception of the superabsorbent polymer material 4 making up the discrete layers 19 of the absorbent pad 2 itself.

In the second and third embodiments, the detecting device 16 is substantially in the shape of a parallelepiped.

The detecting device 16 comprises a top wall 29, a bottom wall 30 and two side walls or flanks 31.

Preferably, the removable element 28 is located along one of the flanks 31 of the detecting device 16.

Preferably, the microwave resonator 21 is located at the top wall 29 of the detecting device 16.

In use, during the passage of the succession of absorbent pads 2 through the slot 25, the detecting device 16 of the second and third embodiments is configured to detect the profile of the discrete absorbent layer 19, preferably step by step.

More specifically, the profile detected is the profile of the discrete absorbent layer 19 along a main longitudinal direction of extension of the absorbent pad 2.

The profile of the discrete absorbent layer 19 defines the position 22 detected by the detecting device 16.

The detecting device 16 sends the detected position 22 to the control and drive unit 17 and the latter compares the position 22 with the reference position 23 and calculates its deviation "d".

If the deviation "d" is such that the valve means 15 are no longer in phase with the drum 10, the control and drive unit 17 drives the actuator unit 20 to reset the valve means 15 in phase with the drum 10.

It should be noted that the position 22 detected by the detecting device 16 is the detection signal 18 of the detecting device 16 and the reference position 23 is the reference signal 19.

Advantageously, the microwave resonator 21 of the detecting device 16 is capable of detecting distinctly one or more absorbent materials 3, 4, 4b defining the absorbent pad 2.

In other words, using the detecting device 16 with the microwave resonator 16 it is possible to detect, distinctly from each other, the weights and density profiles (or weight profiles) of the natural fibre material (fluff) 3, of the superabsorbent polymer material ("SAP") 4 of the first absorbent material 37 and of the superabsorbent polymer material ("SAP") 4b defining the discrete layer 36 of the absorbent pad 2.

During its operation, the microwave resonator 21 emits waves at a certain resonance frequency and, depending on the material inspected, generates a certain resonance curve characterized by a resonance frequency and a mean resonance amplitude.

Since each material is characterized by its own resonance curve, having a specific resonance frequency and a specific mean resonance amplitude, the detecting device 16 is capable of detecting and distinguishing each material making up the inspected object and to calculate its weight and/or density profile (or weight profile).

The control and drive unit 17 is configured to receive from the detecting device 16 at least one between the weight, density profile (or weight profile) parameters of at least one of the absorbent materials 3, 4, 4b of the pad 2 and to compare it with a respective reference parameter.

If the parameter detected by the detecting device 16 deviates from the reference parameter by more than a predetermined threshold value, the control and drive unit 17 is configured to drive, as a function of that deviation, the system 32, 33, 34 for metering the respective absorbent material 3, 4, 4b.

Advantageously, to check the weight and/or density profile (or weight profile) of the discrete layer 36 of superabsorbent polymer material, the control and drive unit 17 is configured to receive from the detecting device 16 at least one between the weight, density profile (or weight profile) parameters of the superabsorbent polymer material 4b defining the discrete layer 36 and to compare it with a respective reference parameter.

If the parameter detected by the detecting device 16 deviates from the reference parameter by more than a predetermined threshold value, the control and drive unit 17 is configured to drive, as a function of that deviation, the third system 34 for metering the respective superabsorbent polymer material 4b.

The correct contribution in weight of the superabsorbent polymer material 4b defining the discrete absorbent layers 36 is fundamental for guaranteeing effective absorption of liquids by the absorbent pad 2.

If the deviation of the detected parameters from the reference parameters is such that the absorbent pad 2 must be considered defective, the control and drive unit 17 is configured to reject the article comprising the defective absorbent pad 2.

This invention also relates to a method for making absorbent pads for nappies which comprise an absorbent pad 2 in turn comprising at least one discrete layer 19 of superabsorbent polymer material 4.

The method comprises a step of feeding along a feed line 5 at least one continuous web 6 of impermeable material and a step of forming and applying a succession 8 of absorbent pads 2 along the continuous web 6 by means of a forming and application unit 7.

The step of forming and applying a succession 8 of absorbent pads 2 comprises a step of feeding a charge of superabsorbent polymer material 4 to a forming drum 10 through a feeding duct 13 comprising valve means 15 driven by a specific actuator unit 20.

The method comprises a step of sending a detection signal 18 indicating that the superabsorbent polymer material 4 has been detected and a step of comparing the detection signal 18 with a reference signal 19.

As a function of the deviation between the detection signal 18 and the reference signal 19, the method comprises a step of driving the actuator unit 20 of the valve means 15 into phase with the drum 10.

More specifically, in a first embodiment, the detection signal 18 indicating that the superabsorbent polymer material 4 has been detected is generated when the charge of superabsorbent polymer material 4 passes in the feeding duct 13 downstream of the valve means 15.

In a second and a third embodiment, the step of sending a detection signal 18 indicating that the superabsorbent polymer material 4 has been detected comprises a step of detecting the position 22 of the discrete layer 19 of superabsorbent polymer material 4 and a step of comparing the detected position 22 with a reference position 23.

The method comprises a step of driving the actuator unit 20 of the valve means 15 into phase with the drum 10 as a function of the deviation between the detected position 22 and the reference position 23.

The method comprises a step of detecting at least one between the weight, density profile (or weight profile) parameters of at least one of the absorbent materials 3, 4, 4*b* defining the absorbent pad 2.

The method further comprises a step of sending at least one between the weight, density profile (or weight profile) parameters of at least one of the absorbent materials 3, 4, 4*b* to a control and drive unit 17 and a step of comparing the detected parameter with a respective reference parameter. A yet further a step of the method comprises driving a system 32, 33, 34 for metering the respective absorbent material as a function of the deviation of the detected parameter from the reference parameter.

The detection step comprises a step of detecting at least one between the weight, density profile (or weight profile) parameters of the superabsorbent polymer material 4*b* defining the discrete layers 36 of the absorbent pad 2.

The method comprises a step of sending at least one between the weight, density profile (or weight profile) parameters of the superabsorbent polymer material 4*b* to a control and drive unit 17 and a step of comparing the detected parameter with a respective reference parameter; and a step of sending a feedback drive signal to a system 34 for metering the superabsorbent polymer material 4*b* defining the discrete layers 36 of the absorbent pad 2 as a function of the deviation of the detected parameter from the reference parameter.

In the first embodiment, the step of detecting at least one between the weight, density profile (or weight profile) parameters of at least one of the absorbent materials 3, 4, 4*b* occurs during the formation of the absorbent pad 2 in the above mentioned unit 7 for forming and applying the succession 8 of absorbent pads 2.

In the second and third embodiments, the step of detecting at least one between the weight, density profile (or weight profile) parameters of at least one of the absorbent materials 3, 4, 4*b* occurs downstream of the unit 7 for forming and applying the absorbent pad 2.

Advantageously, the detecting device 16 makes it possible to detect whether or not the intermittent valve means 15 are in phase with the forming drum 10 and, if they are not in phase, to reset the actuator unit 20 in phase with the forming drum 10 by means of the control and drive unit 17.

Advantageously, detecting the position of the discrete layer 19 of superabsorbent polymer material constituting the discrete layers 19 of the pad 2 by means of the detecting device 16 allows considerable savings in terms of labour cost because it is no longer necessary for an operator to be present at the end of the feed line 5 to check the correct position of the discrete layer 19.

Advantageously, the detecting device 16 comprising a microwave resonator 21 is not affected, in detecting the specified parameters, by external factors such as the temperature and humidity of the operating environment.

Moreover, the microwave resonator 21 allows distinguishing each absorbent material 3, 4, 4*b* defining the pad and to calculate the weight and density profile (or weight profile) of each material.

The invention claimed is:

1. A method for making absorbent sanitary articles which comprise an absorbent pad in turn comprising at least one discrete layer of superabsorbent polymer material; comprising:

feeding at least one continuous web of impermeable material along a feed line;

forming and applying a succession of absorbent pads along the continuous web by a forming and application unit; the forming and applying a succession of absorbent pads comprising feeding a charge of superabsorbent polymer material to a forming drum through a feeding duct comprising a valve device driven by an actuator unit;

sending a detection signal indicating that the superabsorbent polymer material has been detected;

comparing the detection signal with a reference signal; and driving the actuator unit of the valve device into phase with the forming drum;

sending the detection signal when the charge of superabsorbent polymer material passes in the feeding duct downstream of the valve device, and wherein the reference signal is a sync signal of a rotation of the forming drum.

2. The method according to claim 1, wherein the sending the detection signal comprises:

detecting a position of the at least one discrete layer of superabsorbent polymer material;

comparing the detected position with a reference position; and driving the actuator unit of the valve device into phase with the forming drum as a function of a deviation of the detected position from the reference position.

3. The method according to claim 1, and further comprising detecting at least one chosen from a weight parameter, a density profile parameter and a weight profile parameter of the superabsorbent polymer material.

4. The method according to claim 3, and further comprising:

sending the at least one chosen from the weight parameter, the density profile parameter and the weight profile parameter of the superabsorbent polymer material to a control and drive unit;

comparing the detected parameter with a respective reference parameter; and driving a system for metering the superabsorbent polymer material as a function of a deviation of the detected parameter from the reference parameter.

5. The method according to claim 3, and further comprising performing the detecting the at least one chosen from the weight parameter, the density profile parameter and the weight profile parameter of the superabsorbent polymer material downstream of the forming and application unit.

6. The method according to claim 3, and further comprising performing the detecting the at least one chosen from the weight parameter, the density profile parameter and the weight profile parameter of the superabsorbent polymer material during the forming of the succession of absorbent pads in the forming and application unit.

* * * * *